US 10,478,128 B2

(12) United States Patent
Gu et al.

(10) Patent No.: US 10,478,128 B2
(45) Date of Patent: Nov. 19, 2019

(54) HEART RATE DETECTION ARCHITECTURE

(71) Applicant: PixArt Imaging Inc., Hsin-Chu County (TW)

(72) Inventors: Ren-Hau Gu, Hsin-Chu County (TW); Yen-Min Chang, Hsin-Chu County (TW); Ming-Chang Li, Hsin-Chu County (TW); Chih-Hsin Lin, Hsin-Chu County (TW)

(73) Assignee: PIXART IMAGING INC., Hsin-Chu County (TW)

( * ) Notice: Subject to any disclaimer, the term of this patent is extended or adjusted under 35 U.S.C. 154(b) by 0 days.

(21) Appl. No.: 15/819,592

(22) Filed: Nov. 21, 2017

(65) Prior Publication Data
US 2018/0092604 A1 Apr. 5, 2018

Related U.S. Application Data

(63) Continuation-in-part of application No. 14/731,711, filed on Jun. 5, 2015, now Pat. No. 9,974,487.
(Continued)

(30) Foreign Application Priority Data
Sep. 26, 2014 (TW) .............................. 103133698 A

(51) Int. Cl.
*A61B 5/00* (2006.01)
*A61B 5/024* (2006.01)
(Continued)

(52) U.S. Cl.
CPC .......... *A61B 5/721* (2013.01); *A61B 5/02416* (2013.01); *A61B 5/02438* (2013.01);
(Continued)

(58) Field of Classification Search
CPC .......................... A61B 5/02416; A61B 5/0261
See application file for complete search history.

(56) References Cited

U.S. PATENT DOCUMENTS 6,129,676 A 10/2000 Odagiri et al.
7,072,701 B2 7/2006 Chen et al.
(Continued)

OTHER PUBLICATIONS

Fukushiima et al., "Estimating Heart Rate using Wrist-type Photoplethysmography and Acceleration sensor while running", 34th Annual International Conference of the IEEE EMBS, Aug. 28-Sep. 1, 2012, pp. 2901-2904, San Diego, CA, United States, 4pp.

*Primary Examiner* — Hien N Nguyen
(74) *Attorney, Agent, or Firm* — Hauptman Ham, LLP

(57) ABSTRACT

There is provided a system architecture including a PPG hardware module and a MEMS hardware module. The PPG hardware module processes PPG raw data, which is generally composed of analog signals or digital signals. The PPG hardware module filters the raw data for later digital calculation to, for example, find out frequency signals with higher peak values. The PPG hardware module then outputs the selected frequency signals to an MCU for heart rate calculation. The MEMS hardware module receives MEMS raw data from a motion detector made of MEMS elements. The MEMS raw data represents motion status of a user that could possibly affect the heart rate determination result. The MEMS hardware module filters the raw data for later digital calculation to find out frequency signals with higher peak values caused by motion.

15 Claims, 14 Drawing Sheets

Related U.S. Application Data

(60) Provisional application No. 62/503,042, filed on May 8, 2017.

(51) Int. Cl.
 G16H 50/30 (2018.01)
 G16H 40/63 (2018.01)

(52) U.S. Cl.
 CPC ............ A61B 5/725 (2013.01); A61B 5/7257 (2013.01); A61B 5/7275 (2013.01); G16H 40/63 (2018.01); G16H 50/30 (2018.01); A61B 2560/0223 (2013.01); A61B 2562/028 (2013.01); A61B 2562/0219 (2013.01)

(56) References Cited

U.S. PATENT DOCUMENTS

| | | | |
|---|---|---|---|
| 9,848,823 B2* | 12/2017 | Raghuram | A61B 5/486 |
| 2005/0065554 A1* | 3/2005 | KenKnight | A61N 1/3627 |
| | | | 607/4 |
| 2009/0023556 A1 | 1/2009 | Daly et al. | |
| 2010/0113948 A1 | 5/2010 | Yang et al. | |
| 2010/0217099 A1* | 8/2010 | LeBoeuf | A61B 5/00 |
| | | | 600/301 |
| 2010/0268056 A1* | 10/2010 | Picard | A61B 5/0531 |
| | | | 600/388 |
| 2011/0257551 A1 | 10/2011 | Banet et al. | |
| 2014/0275854 A1 | 9/2014 | Venkatraman et al. | |

* cited by examiner

| second frequency domain information I2 | | second frequency domain information I2 | first frequency domain information I1 | | first frequency domain information I1 |
|---|---|---|---|---|---|
| second frequency index | second spectrum value | | first frequency index | first spectrum value | |
| 0 | 20 | | 0 | 45 | |
| 1 | 15 | | 1 | 55 | |
| 2 | 10 | | 2 | 60 | |
| ⋮ | ⋮ | | ⋮ | ⋮ | |
| 25 | 85 | | 25 | 400 | |
| ⋮ | ⋮ | denoising range 20-40 | ⋮ | ⋮ | |
| 28 | 70 | | 28 | 420 | |
| 29 | 65 | | 29 | 410 | |
| 30 | 70 | | 30 | 400 | |
| 31 | 65 | | 31 | 390 | |
| 32 | 60 | | 32 | 400 | |
| ⋮ | ⋮ | P_MAX | ⋮ | ⋮ | |
| 58 | 450 | denoising range 50-70 | 58 | 1770 | |
| 59 | 455 | | 59 | 1790 | |
| 60 | 460 | | 60 | 1800 | |
| 61 | 450 | | 61 | 1780 | |
| 62 | 445 | | 62 | 1760 | |
| ⋮ | ⋮ | | ⋮ | ⋮ | |
| 98 | 46 | | 98 | 870 | |
| 99 | 48 | | 99 | 890 | |
| 100 | 50 | N_HR | 100 | 930 | → P_MAX' |
| 101 | 46 | | 101 | 920 | |
| 102 | 44 | | 102 | 890 | |
| ⋮ | ⋮ | | ⋮ | ⋮ | |
| 118 | 250 | denoising range 110-130 | 118 | 1250 | |
| 119 | 255 | | 119 | 1300 | |
| 120 | 260 | | 120 | 1350 | |
| 121 | 250 | | 121 | 1320 | |
| 122 | 245 | | 122 | 1300 | |
| ⋮ | ⋮ | | ⋮ | ⋮ | |
| 205 | 255 | | 205 | 125 | |
| ⋮ | ⋮ | | ⋮ | ⋮ | |
| 1023 | 1 | | 1023 | 2 | |

Labels on I2: $R_{1/2}$ ← 30; half; R ← 60; double; $R_2$ ← 120

FIG. 6

| three frequency indexes of first frequency domain information I1 |||
|---|---|---|
| N1 = 58 | N2 = 73 | N3 = 117 |

| reference index of second frequency domain information I2 |
|---|
| R = 120 |

| half of reference index and double of reference index ||
|---|---|
| R1/2 = 60 | R2 = 240 |

| denoising range |||
|---|---|---|
| 55~65 | 115~125 | 235~245 |

FIG. 8

HEART RATE DETECTION ARCHITECTURE

CROSS REFERENCE TO RELATED APPLICATION

This application is a continuation-in-part application of U.S. application Ser. No. 14/731,711, filed Jun. 5, 2015, and claims the priority benefit of U.S. Provisional Application Ser. No. 62/503,042, filed on May 8, 2017 and Taiwan Application No. 103133698 filed Sep. 26, 2014, the full disclosures of which are incorporated herein by reference.

BACKGROUND

1. Field of the Invention

This disclosure generally relates to a heart rate detection architecture. More particularly, this disclosure relates to a heart rate detection architecture that integrates PPG data and MEMS data with MCU for heart rate detection.

2. Description of the Related Art

A heart rate detector can calculate the user's heart rate based on photoplethysmography (PPG) signals. However, when the part of a human body being detected has a relative movement with respect to the heart rate detector, a disturbed signal can be detected such that it is difficult to detect a correct heart rate. Therefore, a correct heart rate may not be obtainable under a condition of a non-static state, e.g., especially for the heart rate detector being adapted to portable electronic devices or wearable electronic devices.

SUMMARY

The present disclosure provides a system architecture including a PPG hardware module and a microelectromechanical systems (MEMS) hardware module. The PPG hardware module is configured to process PPG raw data, which is generally composed of analog signals or digital signals. The PPG hardware module is configured to filter the raw data for later digital calculation to, for example, find out frequency signals with higher peak values, e.g., higher than a predetermined amplitude. And the PPG hardware module then outputs the selected frequency signals to MCU for heart rate calculation. The MEMS hardware module is configured to receive MEMS raw data from a motion detector made of MEMS elements. The MEMS raw data represents a motion status of a user that could possibly affect the heart rate determination result. The MEMS hardware module is configured to filter the raw data for later digital calculation to find out frequency signals with higher peak values, e.g., higher than a predetermined amplitude, caused by motion.

The present disclosure further provides a system architecture to output a confidence level parameter of output signals. The confidence level parameter is adapted for later calculation in response to various algorithms. The system architecture is also configured to apply the hardware modules to enter hardware acceleration mode that share a portion of MCU loading.

The present disclosure provides a heart rate detection device including a photoplethysmography (PPG) hardware module, a microelectromechanical systems (MEMS) hardware module and a microcontroller unit (MCU). The PPG hardware module is configured to receive PPG raw data and generate PPG frequency data. The MEMS hardware module is configured to receive MEMS raw data and generate MEMS frequency data. The MCU is electrically coupled to the PPG hardware module and the MEMS hardware module, and configured to estimate a heart rate according to the PPG frequency data in referencing the MEMS frequency data.

The present disclosure further provides a heart rate detection device configured to receive a photoplethysmography (PPG) raw data from a PPG detector and a microelectromechanical systems (MEMS) raw data from a MEMS accelerometer. The heart rate detection device includes a PPG hardware module and a MEMS hardware module. The PPG hardware module is configured to receive the PPG raw data and includes a first bandpass filter, a first conversion module and a first peak extraction module. The first bandpass filter is configured to filter the PPG raw data. The first conversion module is configured to convert the filtered PPG raw data to PPG frequency data. The first peak extraction module is configured to search PPG peak values among the PPG frequency data, and output the PPG peak values and the PPG frequency data. The MEMS hardware module is configured to receive the MEMS raw data and includes a second bandpass filter, a second conversion module and a second peak extraction module. The second bandpass filter is configured to filter the MEMS raw data. The second conversion module is configured to convert the filtered MEMS raw data to MEMS frequency data. The second peak extraction module is configured to search MEMS peak values among the MEMS frequency data, and output the MEMS peak values and the MEMS frequency data.

BRIEF DESCRIPTION OF THE DRAWINGS

Other objects, advantages, and novel features of the present disclosure will become more apparent from the following detailed description when taken in conjunction with the accompanying drawings.

FIG. 6 is a schematic diagram of first frequency domain information and second frequency domain information according to one embodiment of the present disclosure.

FIG. 8 is a schematic diagram of frequency indexes, a reference index and a denoising range according to one embodiment of the present disclosure.

DETAILED DESCRIPTION OF THE EMBODIMENT

It should be noted that, wherever possible, the same reference numbers will be used throughout the drawings to refer to the same or like parts.

The present disclosure provides a heart rate detection module with a denoising function and adaptable to a smart watch, a wristband, glasses, a wearable device or a portable device, but not limited thereto. In some embodiments, the wearable device or the portable device may or may not have a display function. In some embodiments, the heart rate detection module is an individual detection device and is attached to the devices in an appropriate manner while being used so as to improve the usability thereof.

Figure 1:
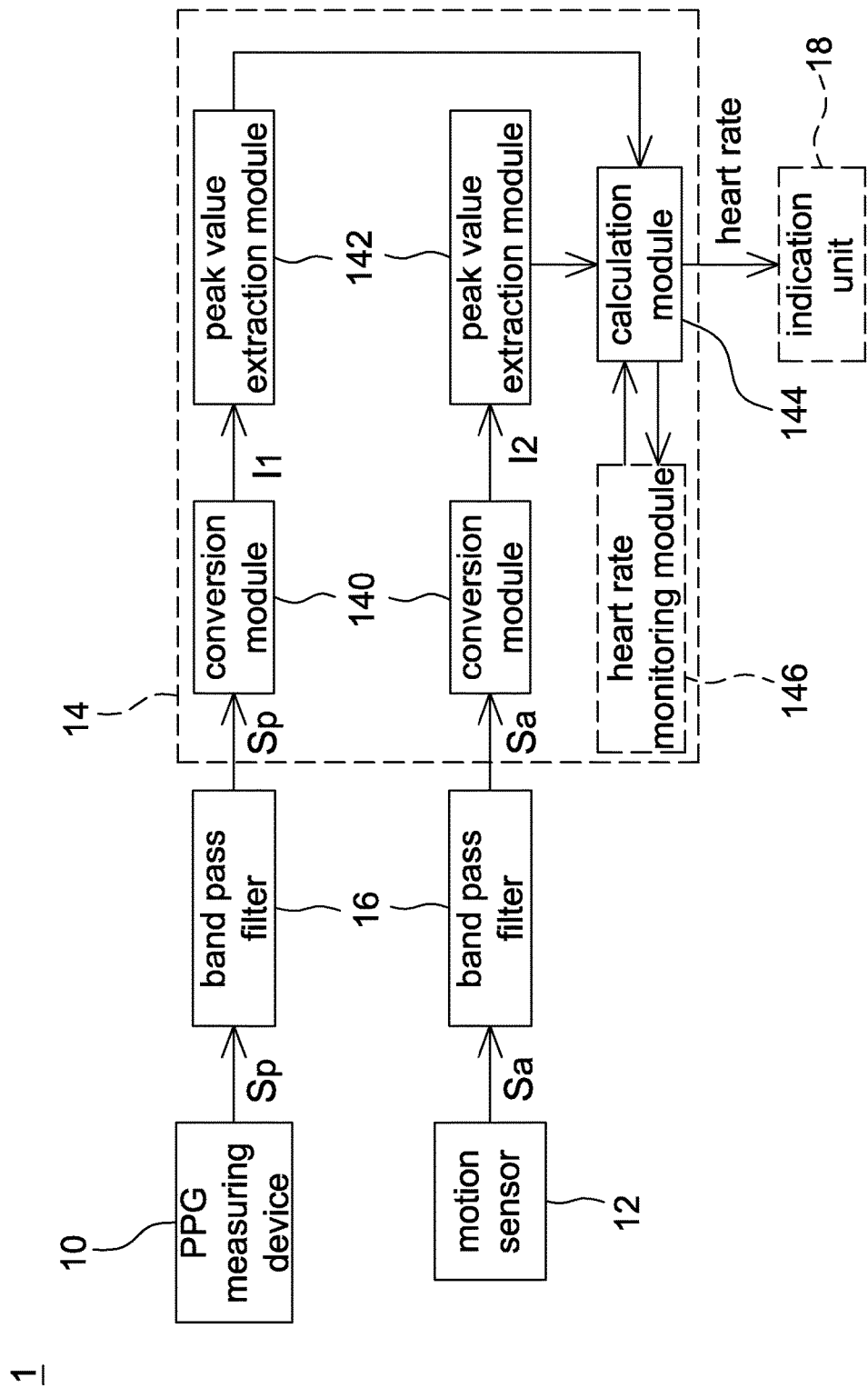
FIG. 1 is a schematic block diagram of a heart rate detection module according to one embodiment of the present disclosure.

Referring to FIG. 1, it is a schematic block diagram of a heart rate detection module 1 according to one embodiment of the present disclosure. The heart rate detection module 1 includes a photoplethysmography (PPG) measuring device 10, a motion sensor 12 and a processing unit 14, wherein the processing unit 14 includes a conversion module 140, a peak value extraction module 142 and a calculation module 144. In some embodiments, two band pass filters 16 are respectively disposed between the PPG measuring device 10 and the processing unit 14 and between the motion sensor 12 and the processing unit 14. In some embodiments, the processing unit 14 further includes a heart rate monitoring module 146 configured to record heart rates calculated by the calculation module 144. It is appreciated that a power module (not shown) is electrically connected to the heart rate detection module 1 for providing power required by the heart rate detection module 1 in operation.

The PPG measuring device 10 is configured to detect a skin surface in a detection period to output a PPG signal $S_p$. Generally speaking, the PPG measuring device 10 has a light emitting module and a sensing region. The PPG measuring device 10 is a reflective PPG measuring device or a transmissive PPG measuring device without particularly limitations. The method for the PPG measuring device 10 to generate the PPG signal $S_p$ according to detected light signals is known to the art and thus details thereof are not described herein. A location of the skin surface to be detected by the PPG measuring device 10 is not particularly limited and is determined according to an electronic device to which the heart rate detection module 1 adapted.

The motion sensor 12 is, for example, a gyroscope, an accelerometer, a G sensor or other devices configured to sense human body movement. In this embodiment, the motion sensor 12 is illustrated by taking an accelerometer as an example. The motion sensor 12 is configured to output an acceleration signal $S_a$ corresponding to the detection period of the PPG measuring device 10 so that the acceleration signal $S_a$ has a corresponding relationship with the PPG signal $S_p$. In one embodiment, the motion sensor 12 is manufactured by microelectro-mechanical systems (MEMS) technology.

Figure 2A:
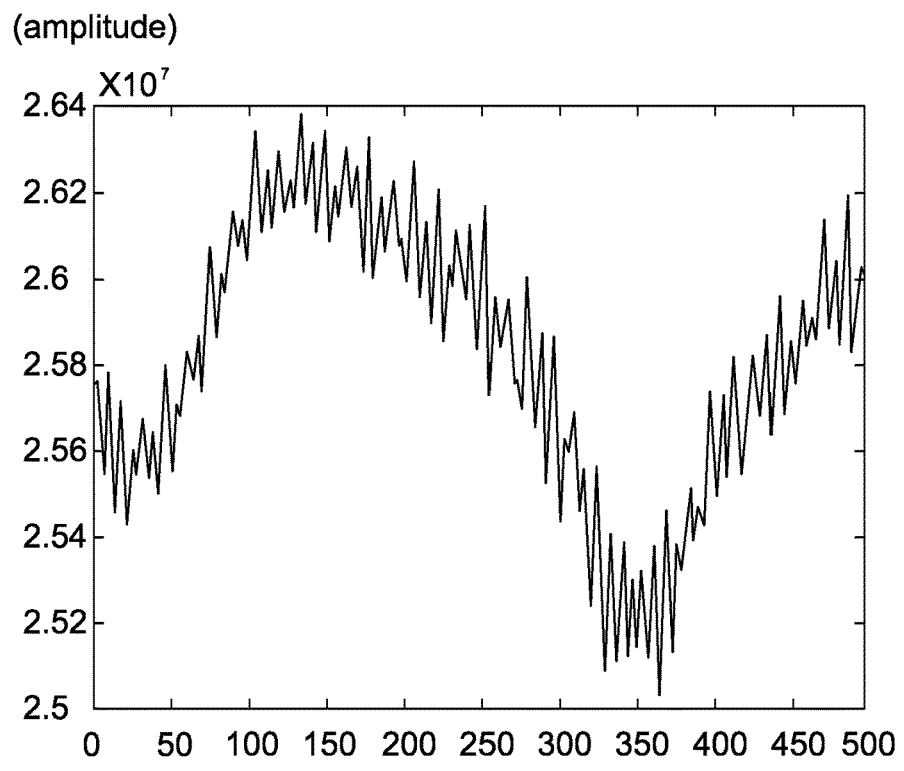
FIG. 2A is a schematic diagram of a PPG signal before being filtered according to one embodiment of the present disclosure.
Figure 2B:
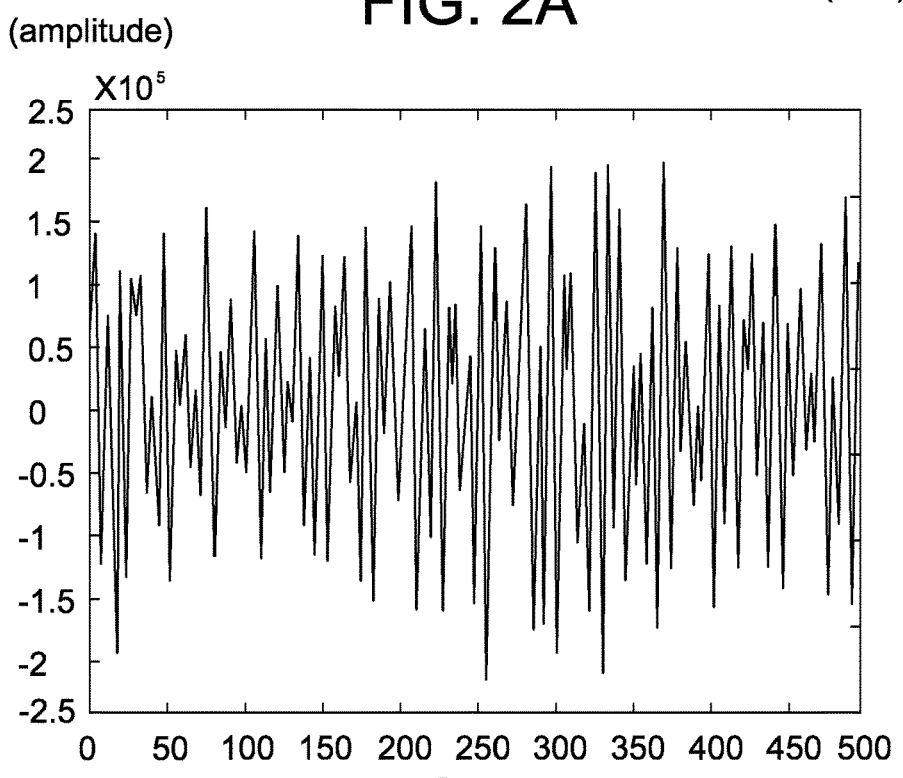
FIG. 2B is a schematic diagram of a PPG signal after being filtered according to one embodiment of the present disclosure.

In this embodiment, the heart rate detection module 1 has two band pass filters 16 respectively between the PPG measuring device 10 and the processing unit 14 and between the motion sensor 12 and the processing unit 14, and the two band pass filters 16 are respectively configured to filter the PPG signal $S_p$ and the acceleration signal $S_a$. For example, FIGS. 2A and 2B are schematic diagrams of the PPG signal $S_p$ before and after being filtered by the band pass filter 16, wherein the x-axis indicates the time and the y-axis indicates the amplitude. Generally speaking, a human heart rate is between 30 beats/min and 240 beats/min, and a signal frequency range of the human heart rate is from 0.5 Hz to 4 Hz since a heart rate of 60 beats/min corresponds to 1 Hz. Therefore, a passband of the band pass filters 16 is selected, for example, from 0.5 Hz to 4 Hz or from 0.45 Hz to 4.5 Hz so as to improve the signal quality of the PPG signal $S_p$ and the acceleration signal $S_a$ (i.e. filtering frequencies not related to the human heart rate), but not limited thereto. To simplify the description, the PPG signal and the acceleration signal after being filtered by the band pass filters 16 are also indicated by reference numbers $S_p$ and $S_a$, respectively.

It should be mentioned that although the band pass filters 16 are not included in the processing unit 14 in FIG. 1, the present disclosure is not limited thereto. In some embodiments, the band pass filters 16 are respectively disposed in the PPG measuring device 10 and the motion sensor 12. In some embodiments, the band pass filters 16 are disposed in the processing unit 14.

The processing unit 14 is, for example, a digital signal processor (DSP) or other processing devices for processing signals, and processing functions thereof are implemented by software, hardware or firmware. The processing unit 14 is configured to eliminate, according to the acceleration signal $S_a$, noise in the PPG signal $S_p$ generated by relative movements between the sensing region of the PPG measuring device 10 and the skin surface. For example, in some embodiments, the processing unit 14 converts the PPG signal $S_p$ and the acceleration signal $S_a$ respectively to first frequency domain information $I_1$ and second frequency domain information $I_2$, determines a denoising parameter according to a maximum spectrum peak value of the second frequency domain information $I_2$ to denoise the first frequency domain information $I_1$, and calculates a heart rate according to a maximum spectrum peak value of the denoised first frequency domain information.

The conversion module 140 of the processing unit 14 is configured to convert the PPG signal $S_p$ to a frequency domain PPG signal, generate a first frequency index set and a first spectrum value set associated with the first frequency index set configured as the first frequency domain information $I_1$, convert the acceleration signal $S_a$ to a frequency domain acceleration signal, and generate a second frequency index set and a second spectrum value set associated with the second frequency index set configured as the second frequency domain information $I_2$.

The peak value extraction module 142 of the processing unit 14 is configured to identify a plurality of spectrum peak values in the first frequency domain information $I_1$ and the second frequency domain information $I_2$, and output frequency indexes corresponding to the plurality of spectrum peak values to the calculation module 144.

The calculation module 144 of the processing unit 14 is configured to eliminate noise in the first frequency domain information $I_1$ according to the frequency indexes corresponding to the plurality of spectrum peak values and then calculate the heart rate (described later).

The heart rate monitoring module 146 is configured to record a variation tendency of heart rates corresponding to a plurality of the detection periods so that when the calculation module 144 is unable to directly calculate a heart rate according to the denoised first frequency domain information, the heart rate is further estimated according the variation tendency (described later).

It is appreciated that the conversion module 140, the peak value extraction module 142, the calculation module 144 and the heart rate monitoring module 146 of this embodiment indicate function blocks or program instructions inside the processing unit 14. It is appreciated that in other embodiments, the conversion module 140, the peak value extraction module 142, the calculation module 144 and the heart rate monitoring module 146 may be implemented by different processing units. It should be mentioned that two conversion modules 140 and two peak value extraction modules 142 are shown in FIG. 1, but the present disclosure is not limited thereto. The processing unit 14 may include only one conversion module 140 and only one peak value extraction module 142.

In some embodiments, the heart rate detection module 1 further includes an indication unit 18, e.g. a speaker or a display, configured to represent the heart rate through audio or images. In this case, the power module further provides power required by the indication unit 18.

In some embodiments, the indication unit 18 is not included in the heart rate detection module 1. For example, when the heart rate detection module 1 is integrated with a smart band, the indication unit 18 may be a display screen of a smart phone. In this case, the heart rate detection module 1 transmits a signal containing the heart rate information from the smart band to the smart phone in a wireless manner (e.g. Bluetooth, Wi-Fi, ZigBee or other wireless communication protocols) to show the heart rate and the variation tendency thereof in real time.

In some embodiments, the indication unit 18 is disposed in a computer system connected to a cloud system. In this case, the heart rate detection module 1 transmits a signal containing the heart rate information to the cloud system in a wireless manner for the cloud system to record the heart rate. In therapeutic applications, a medical staff may monitor the user's heart rate through the computer system.

It is appreciated that the heart rate detected by the heart rate detection module 1 may be used for different applications. In the present disclosure, it is to eliminate signal noise in the PPG signal by using the acceleration signal so as to improve the accuracy of calculating the heart rate.

Figure 3:
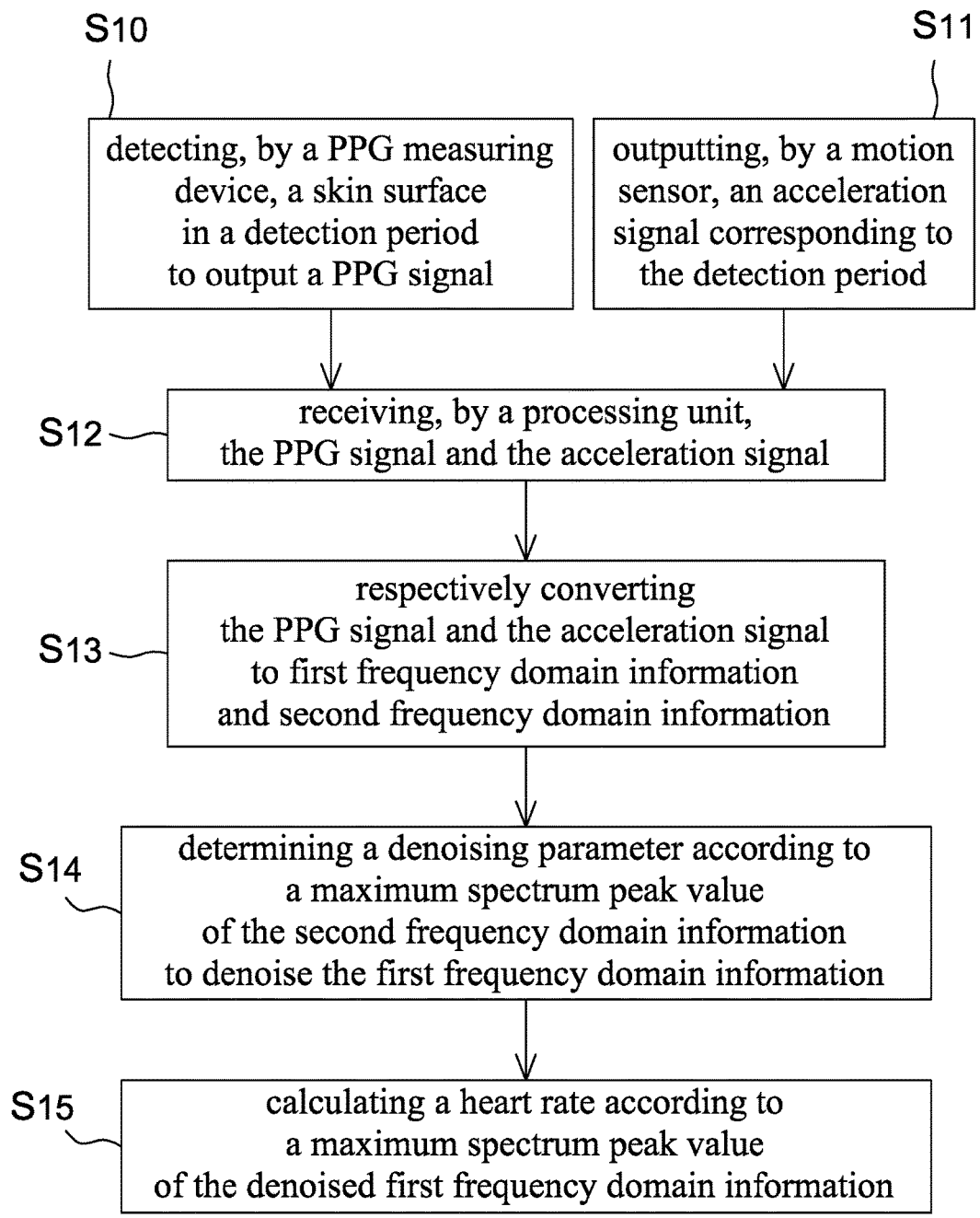
FIG. 3 is a flow chart of a heart rate detection method according to one embodiment of the present disclosure.

FIG. 3 is a flow chart of a heart rate detection method according to one embodiment of the present disclosure. The heart rate detection method includes the steps of: detecting, by a PPG measuring device, a skin surface in a detection period to output a PPG signal (Step $S_{10}$); outputting, by a motion sensor, an acceleration signal corresponding to the detection period (Step $S_{11}$); receiving, by a processing unit, the PPG signal and the acceleration signal (Step $S_{12}$); respectively converting the PPG signal and the acceleration signal to first frequency domain information and second frequency domain information (Step $S_{13}$); determining a denoising parameter according to a maximum spectrum peak value of the second frequency domain information to denoise the first frequency domain information (Step $S_{14}$); and calculating a heart rate according to a maximum spectrum peak value of the denoised first frequency domain information (Step $S_{15}$).

Figures 4A, 4B:
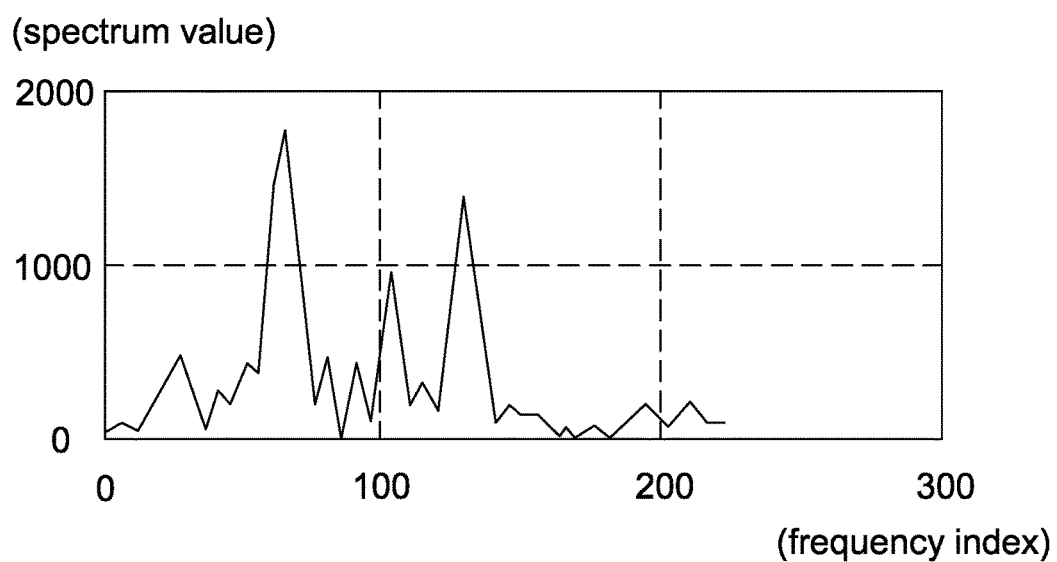
FIG. 4A is a spectrum diagram of a frequency domain PPG signal according to one embodiment of the present disclosure.
FIG. 4B is a schematic diagram of first frequency domain information corresponding to the spectrum diagram of FIG. 4A.
Figures 5A, 5B:
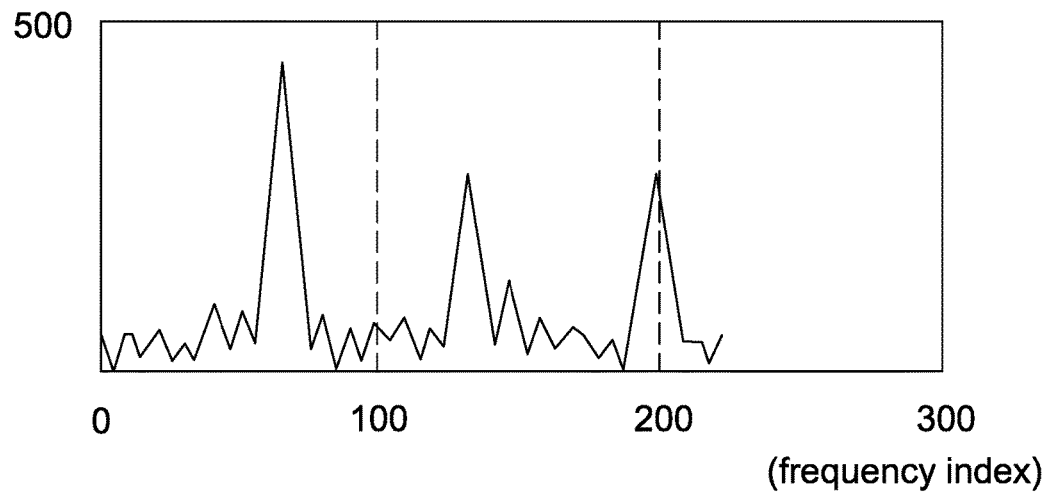
FIG. 5A is a spectrum diagram of a frequency domain acceleration signal according to one embodiment of the present disclosure.
FIG. 5B is a schematic diagram of second frequency domain information corresponding to the spectrum diagram of FIG. 5A.

Referring to FIGS. 1, 3, 4A, 4B, 5A, 5B and 6 together, details of this embodiment are described hereinafter, wherein FIGS. 4A and 4B are respectively a spectrum diagram of a frequency domain PPG signal and a schematic diagram of first frequency domain information according to one embodiment of the present disclosure, FIGS. 5A and 5B are respectively a spectrum diagram of a frequency domain acceleration signal and a schematic diagram of second frequency domain information according to one embodiment of the present disclosure, and FIG. 6 is a schematic diagram of the first frequency domain information and the second frequency domain information according to one embodiment of the present disclosure. It is appreciated that FIGS. 4A, 4B, 5A, 5B and 6 are only intended to illustrate, but not to limit the present disclosure.

Step $S_{10}$ to $S_{11}$: Firstly, a PPG measuring device 10 of a heart rate detection module 1 detects a skin surface in a detection period to output a PPG signal $S_p$. Meanwhile, a motion sensor 12 outputs an acceleration signal $S_a$ corresponding to the detection period. To simplify the description, the PPG signal $S_p$ and the acceleration signal $S_a$ in the following descriptions may indicate signals filtered by the band pass filters 16 without further indications. It should be mentioned that since the acceleration signal $S_a$ is mainly used to eliminate noise in the PPG signal $S_p$ generated by relative movements between a sensing region of the PPG measuring device 10 and the skin surface, preferably the PPG signal $S_p$ and the acceleration signal $S_a$ are related to substantially identical detection periods so that the heart rate detection module 1 may denoise information related to the PPG signal $S_p$ according to information related to the acceleration signal $S_a$ in calculating the heart rate.

Step $S_{12}$: Then, the processing unit 14 receives the PPG signal $S_p$ and the acceleration signal $S_a$ together for post processing. As shown in FIG. 1, the PPG signal $S_p$ and the acceleration signal $S_a$ are respectively inputted to a conversion module 140 of the processing unit 14.

Step $S_{13}$: The conversion module 140 of the processing unit 14 converts the PPG signal $S_p$ to a frequency domain PPG signal and generate a first frequency index set and a first spectrum value set associated with the first frequency index set, wherein each frequency index corresponds to one spectrum value. It should be mentioned that the conversion module 140 of this embodiment may use Fast Fourier Transform (FFT) to convert the PPG signal $S_p$ from time domain to frequency domain to generate the frequency domain PPG signal, but the present disclosure is not limited thereto. In other embodiments, the conversion module 140 may use Discrete Fourier Transform (DFT) or other time domain to frequency domain conversion methods (i.e. spectrum analysis) to convert the PPG signal $S_p$.

It should be mentioned that the frequency domain PPG signal is a discrete signal so that the processing unit 14 is able to perform digital signal processing accordingly. In some embodiments, when the PPG signal $S_p$ outputted by the PPG measuring device 10 is a continuous time domain signal, the conversion module 140 firstly converts the PPG signal $S_p$ to a discrete time domain signal (e.g. by sampling the PPG signal $S_p$ with a sampling frequency), and then converts the discrete time domain signal to a discrete frequency domain signal accordingly, but not limited thereto. In other embodiments, the conversion module 140 firstly converts the PPG signal $S_p$ to a continuous frequency domain signal, and then converts the continuous frequency domain signal to a discrete frequency domain signal accordingly.

As mentioned above, a signal frequency range of the human heart rate is from 0.5 Hz to 4 Hz. It is assumed that a maximum value of the signal frequency of the human heart rate is 4 Hz (corresponding to 240 beats/min), and a sampling frequency has to be larger than 8 Hz (e.g. 10 Hz or 20 Hz) so that Nyquist theorem is satisfied. In one embodiment in using FFT, the sampling frequency is 20 Hz, but not limited thereto. The sampling frequency is determined according to operating capability of the processing unit 14.

After the conversion module 140 uses FFT to convert the PPG signal $S_p$ to the frequency domain PPG signal, a spectrum diagram corresponding to the frequency domain PPG signal is generated, as shown in FIG. 4A, wherein the x-axis of the spectrum diagram indicates the frequency index of FFT and the y-axis indicates the spectrum amplitude. In this embodiment, frequency indexes and spectrum amplitudes corresponding to the frequency indexes in FIG. 4A are respectively configured as a first frequency index set and a first spectrum value set associated with the first frequency index set, i.e. first frequency domain information $I_1$, as shown in FIG. 4B.

It should be mentioned that a number of the frequency indexes of FFT is, for example, 1024 bins, but not limited thereto, wherein each of the frequency indexes corresponds to one frequency. For example, a frequency corresponding to a frequency index 256 is (20 Hz/1024)×256=5 Hz. It is appreciated that when the sampling frequency is 20 Hz and the number of the frequency indexes is 1024 bins, a frequency resolution of the first frequency domain information $I_1$ is about 20 Hz/1024=0.0195 Hz. When the sampling frequency is a fixed value and the number of the frequency indexes is higher, a frequency difference between two adjacent frequency indexes becomes smaller so that the heart rate detection module 1 has a higher sensitivity in calculating the heart rate according to the frequency indexes.

It should be mentioned that since the human heart rate is between 30 beats/min and 240 beats/min, a frequency index range corresponding to the human heart rate in the first frequency domain information $I_1$ is substantially from 25 to 205. Therefore, in some embodiments, the processing unit 14 removes (or releases) frequency indexes smaller than 25 and/or larger than 205 and the associated spectrum values for saving system resources, but not limited thereto.

Similarly, another conversion module 140 in the processing unit 14 uses the same way as converting the PPG signal $S_p$ to convert the acceleration signal $S_a$ to generate a spectrum diagram corresponding to the frequency domain acceleration signal, as shown in FIG. 5A, and generate a second frequency index set and a second spectrum value set associated with the second frequency index set configured as second frequency domain information $I_2$, as shown in FIG. 5B. In some embodiments, in the second frequency domain information $I_2$, only frequency indexes within the frequency index range (e.g. from 25 to 205) and the associated spectrum values are reserved.

Step $S_{14}$: After the second frequency domain information $I_2$ is obtained, the peak value extraction module 142 determines a reference index R according to a frequency index corresponding to a maximum spectrum peak value $P_{MAX}$ in the second frequency domain information $I_2$. For example, referring to FIG. 6, it is assumed that a maximum spectrum peak value is 460 in the second frequency domain information $I_2$. In this case, the peak value extraction module 142 identifies that the maximum spectrum peak value $P_{MAX}$ is 460 and outputs a frequency index 60 corresponding to the maximum spectrum peak value $P_{MAX}$ to the calculation module 144 configured as the reference index R. Then, the calculation module 144 calculates a half of the reference index R and a double of the reference index R. For example, when the reference index R is 60, the half of reference index $R_{1/2}$ is 30 and the double of reference index $R_2$ is 120. It is appreciated that since each of the frequency indexes indicates one frequency, a frequency corresponding to the double of reference index $R_2$ is a double of the frequency corresponding to the reference index R, and a frequency corresponding to the half of reference index $R_{1/2}$ is a half of the frequency corresponding to the reference index R.

Meanwhile, the calculation module 144 determines a denoising parameter according to the reference index R and at least one of the half of reference index $R_{1/2}$ and the double of reference index $R_2$ to denoise the first spectrum value set. For example, the denoising parameter may contain the reference index R and the half of reference index $R_{1/2}$, contain the reference index R and the double of reference index $R_2$, or contain the reference index R, the half of reference index $R_{1/2}$ and the double of reference index $R_2$. Denoising the first spectrum value set is referred to remove spectrum values in the first frequency domain information $I_1$ corresponding to the reference indexes and nearby reference indexes according to the denoising parameter obtained by the reference index R. For example, when the reference indexes $R_{1/2}$, R and $R_2$ are 30, 60 and 120 respectively, the processing unit 14 may determine, by respectively plus and minus a predetermined range to and from the reference indexes, a denoising range as 20 to 40, 50 to 70 and 110 to 130 (i.e. 30±10, 60±10 and 120±10), and remove spectrum values in the first spectrum value set associated with the denoising range configured as a method to denoise the first frequency domain information $I_1$. In some embodiments, the predetermined range is set before the shipment of the heart rate detection module 1 or in the initialization of the heart rate detection module 1.

In addition, since the second frequency domain information $I_2$ is configured for the processing unit 14 to determine the denoising parameter, in some embodiments, the processing unit 14 removes (or releases) the second frequency domain information 12 for saving system resources after the calculation module 144 obtains the maximum spectrum peak value $P_{MAX}$ from the peak value extraction module 142 or after the denoising parameter is determined, but not limited thereto.

Step $S_{15}$: Finally, the calculation module 144 calculates a heart rate according to a maximum spectrum peak value of the denoised first frequency domain information. More specifically speaking, when the maximum spectrum peak value in the first frequency domain information $I_1$ is identified, the calculation module 144 removes spectrum values corresponding to the denoising range (i.e. spectrum values in the first frequency index set corresponding to the frequency indexes 20 to 40, 50 to 70 and 110 to 130). For example, after spectrum values corresponding to the denoising range are removed according to the embodiment of FIG. 6 (e.g. areas with oblique lines indicating the range of the spectrum values to be removed), the maximum spectrum peak value of the denoised first frequency domain information is determined as 930 (i.e. a denoised maximum spectrum peak value $P_{MAX}'$). The calculation module 144 then calculates a heart rate according to a frequency index (i.e. 100) corresponding to the denoised maximum spectrum peak value $P_{MAX}'$. As mentioned above, the heart rate is (20/1024)×100× 60=117.19 beats/min since a heart rate of 60 beats/min corresponds to 1 Hz. Accordingly, even if the PPG measuring device 10 outputs a PPG signal containing disturbed waveform in a non-static state, the heart rate detection module 1 is still able to calculate an accurate heart rate according to the above steps.

It should be mentioned that in this embodiment, the calculation module 144 only removes (or ignores) spectrum values in the first frequency domain information $I_1$ corresponding to the denoising parameter but not to directly delete the spectrum values from a memory in identifying the maximum spectrum peak value of the first frequency domain information $I_1$ (e.g. in calculating the heart rate), but the present disclosure is not limited thereto. In some embodiments, before the step $S_{15}$ or after the denoising parameter is determined, the processing unit 14 may remove frequency indexes and spectrum values in the first frequency domain information $I_1$ corresponding to the denoising parameter from the memory in advance for saving system resources.

On the other hand, to improve the accuracy of calculating the heart rate, in some embodiments, the processing unit 14 takes a frequency index corresponding to the maximum spectrum peak value (e.g. $P_{MAX}'$) of the denoised first frequency domain information as a heart rate index $N_{HR}$ (e.g. 100). Then, a heart rate is calculated according to the heart rate index $N_{HR}$ and frequency indexes adjacent to the heart rate index $N_{HR}$. For example, referring to FIG. 6 again, when the heart rate index $N_{HR}$ is 100, the heart rate detection module 1 calculates an energy center as (99×890+100×930+101×920)/(890+930+920)=100.011 according to the heart rate index $N_{HR}$, two frequency indexes 99 and 101 adjacent to the heart rate index $N_{HR}$, and spectrum values 930, 890 and 920 respectively corresponding thereto. Then, the calculation module 144 calculates the heart rate as (20/1024)×100.011×60=117.20 beats/min according to the energy center, but not limited thereto. The calculation module 144 may calculate the heart rate according to the heart rate index and a plurality of frequency indexes (e.g. 4 or 6 frequency indexes) adjacent to the heart rate index.

Since the heart rate detection module 1 calculates one heart rate in each detection period, the heart rate detection module 1 may calculate, according to heart rates of a plurality of detection periods, a variation tendency of the heart rates of the plurality of detection periods to estimate a heart rate accordingly. In some embodiments, the processing unit 14 further includes a heart rate monitoring module 146 configured to record a variation tendency of the heart rates corresponding to a plurality of the detection periods. For example, in the embodiment of FIG. 6, after a user exercises for a period (wherein the period is, for example, longer than at least twice of the detection period), it is assumed that the denoising range is not changed and the heart rate index $N_{HR}$ varies from 100 to 110. As the calculation module 144 may ignore spectrum values corresponding to the denoising range (i.e. spectrum values corresponding to the frequency indexes 110 to 130 in the first frequency index set) when identifying the maximum spectrum peak value in the first frequency domain information $I_1$, the heart rate index $N_{HR}$ will be ignored in this case, and the calculation module 144 further estimates a current heart rate according to the variation tendency (e.g. a tendency that the heart rate index $N_{HR}$ varies from 100 to 110 during the period) recorded by the heart rate monitoring module 146.

In one aspect according to the embodiment of FIG. 6, when the heart rate index $N_{HR}$ gradually varies from 100 to 110, the calculation module 144 partially ignores spectrum values corresponding to the denoising range, e.g. ignoring spectrum values corresponding to the frequency indexes 20 to 40 and 50 to 70 but not ignoring spectrum values corresponding to the frequency indexes 110 to 130 in the first frequency index set. That is to say, the calculation module 144 takes the denoising range 110 to 130 as an invalid denoising range according to a variation of the heart rate index $N_{HR}$. In this case, the calculation module 144 calculates the heart rate according to the heart rate index $N_{HR}$ or a maximum spectrum peak value of the denoised first frequency domain information (e.g. a frequency index 120 corresponding to the spectrum value 1350 in the first spectrum value set).

Figure 7:
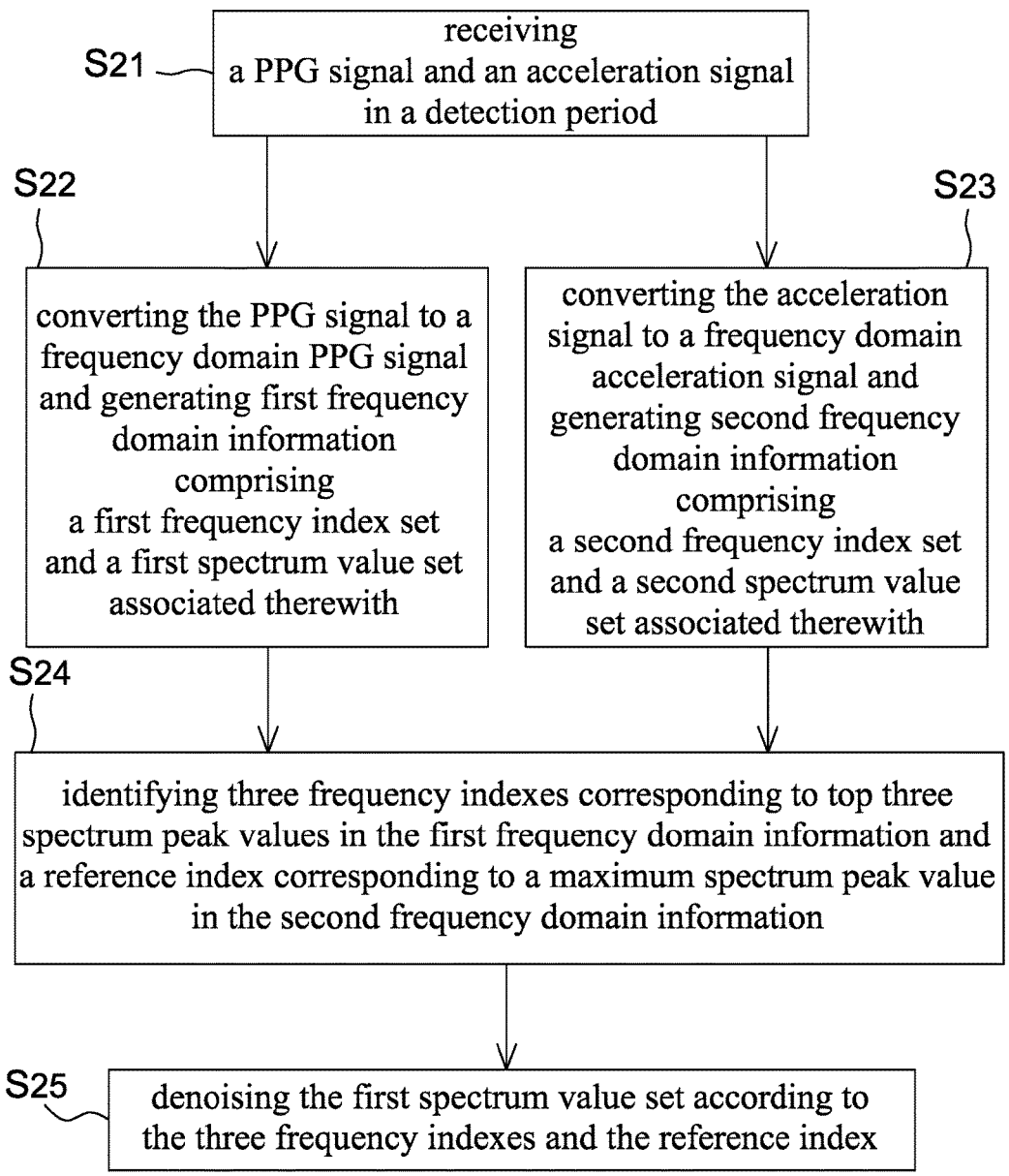
FIG. 7 is a flow chart of a denoising method according to one embodiment of the present disclosure.

FIG. 7 is a flow chart of a denoising method according to one embodiment of the present disclosure. The denoising method includes the steps of: receiving a PPG signal and an acceleration signal in a detection period (Step $S_{21}$); converting the PPG signal to a frequency domain PPG signal and generating first frequency domain information containing a first frequency index set and a first spectrum value set associated therewith (Step $S_{22}$); converting the acceleration signal to a frequency domain acceleration signal and generating second frequency domain information containing a second frequency index set and a second spectrum value set associated therewith (Step $S_{23}$); identifying three frequency indexes corresponding to top three spectrum peak values in the first frequency domain information and a reference index corresponding to a maximum spectrum peak value in the second frequency domain information (Step $S_{24}$); and denoising the first spectrum value set according to the three frequency indexes and the reference index (Step $S_{25}$).

Referring to FIGS. 1, 6, 7 and 8 together, details of this embodiment are described hereinafter, wherein FIG. 8 is a schematic diagram of frequency indexes, a reference index and a denoising range according to one embodiment of the present disclosure.

Step $S_{21}$: Firstly, a PPG signal $S_p$ and an acceleration signal $S_a$ are received in a detection period. It is appreciated that the PPG signal $S_p$ and the acceleration signal $S_a$ are, for example, respectively outputted from a PPG measuring device 10 and a motion sensor 12, as shown in FIG. 1.

Step $S_{22}$: Then, the PPG signal $S_p$ is converted to a frequency domain PPG signal by using FFT or other time domain to frequency domain conversion methods, and first frequency domain information $I_1$ containing a first frequency index set and a first spectrum value set associated with the first frequency index set is generated, as shown in FIG. 6.

Step $S_{23}$: The acceleration signal $S_a$ is converted to a frequency domain acceleration signal by using the same method as converting the PPG signal $S_p$, and second frequency domain information $I_2$ containing a second frequency index set and a second spectrum value set associated with the second frequency index set is generated. In this embodiment, since the heart rate detection module 1 includes two independent conversion modules 140, the steps $S_{23}$ and $S_{22}$ may be performed at the same time, but not limited thereto.

It is appreciated that a processing unit 14 may reserve required information of frequency indexes and spectrum values in the first frequency domain information $I_1$ and the second frequency domain information $I_2$ and store in a memory unit, e.g. only reserving the frequency indexes 0 to 225 and spectrum values associated therewith, but not limited thereto.

Step $S_{24}$: After the first frequency domain information $I_1$ and the second frequency domain information $I_2$ are obtained, the processing unit 14 identifies three frequency indexes $N_1$, $N_2$ and $N_3$ corresponding to top three spectrum peak values in the first frequency domain information $I_1$ and a reference index R corresponding to a maximum spectrum peak value in the second frequency domain information $I_2$. For example, the three frequency indexes $N_1$, $N_2$ and $N_3$ corresponding to the top three spectrum peak values in the first frequency domain information $I_1$ are respectively 58, 73 and 117, and the reference index R corresponding to the maximum spectrum peak value in the second frequency domain information $I_2$ is 120, as shown in FIG. 8.

Step $S_{25}$: Finally, the processing unit 14 calculates a half of frequency index $R_{1/2}$ and/or a double of frequency index $R_2$ as 60 and 240, and determines a denoising range, wherein the denoising range is, for example, determined by plus and minus 5 to and from the reference indexes $R_{1/2}$, R and $R_2$, as 55 to 65, 115 to 125 and 235 to 245, as shown in FIG. 8. Accordingly, the processing unit 14 denoises the frequency domain PPG signal according to the denoising range determined by the three frequency indexes $N_1$ to $N_3$ and the reference index R.

As mentioned above, in a non-static state, the PPG measuring device 10 may output incorrect PPG signals so that the processing unit 14 may not directly calculate a correct heart rate according to the PPG signal. Therefore, after the denoising range is determined through the steps $S_{21}$ to $S_{25}$ of this embodiment, spectrum values in the first frequency domain information $I_1$ associated with frequency indexes within the denoising range may be noise, and the processing unit 14 may remove frequency indexes in the first frequency domain information $I_1$ within the denoising range or spectrum values associated with the frequency indexes so as to denoise the first frequency domain information $I_1$.

In one application, the denoising method is adapted to, for example, calculate a heart rate. Referring to FIG. 8 again, when the frequency indexes $N_1$ and $N_3$ of the first frequency domain information $I_1$ is in the denoising range (i.e. 58 and 117 are respectively between 55 to 65 and 115 to 125) and the frequency index $N_2$ is not in the denoising range, the processing unit 14 may determine a heart rate index $N_{HR}$ as 73 (i.e. the frequency index $N_2$) among the three frequency indexes $N_1$, $N_2$ and $N_3$ according to the denoising range. Then, the processing unit 14 calculates a heart rate according to the heart rate index $N_{HR}$. For example, the heart rate is (20/1024)×73×60=85.55 beats/min. In some embodiment, the processing unit 14 calculates a heart rate according to the heart rate index $N_{HR}$ and frequency indexes adjacent to the heart rate index $N_{HR}$. The calculation method thereof is described above and thus details thereof are not repeated herein.

It should be mentioned that the denoising range is based on the frequency indexes $N_1$ to $N_3$ and generated by plus and minus a predetermined range (i.e. 5) to and from the frequency indexes $N_1$ to $N_3$, wherein the predetermined range may or may not be related to a sampling frequency of the conversion module 140 and a number of the frequency indexes. As mentioned above, a frequency resolution is determined by the sampling frequency and the number of the frequency indexes. In some embodiments, the predetermined range is inversely correlated with the frequency resolution, but not limited thereto.

In some embodiments, the processing unit 14 further determines two residual indexes as 58 and 117 (i.e. the frequency indexes $N_1$ and $N_3$) among the three frequency indexes $N_1$ to $N_3$ according to the denoising range. It is assumed that the denoising range and the residual indexes $N_1$ and $N_3$ are not changed. After a user exercises for a period, since the user's heart rate rises, the frequency index $N_2$ associated with the heart rate is gradually approaching the frequency index $N_3$ so that the frequency index $N_2$ falls into the denoising range (i.e. the frequency indexes 115 to 125). In this case, the processing unit 14 may not determine the heart rate index $N_{HR}$ among the three frequency indexes $N_1$ to $N_3$ according to the denoising range. Therefore, when a difference value between the heart rate index $N_{HR}$ (e.g. the frequency index $N_2$) and one of the residual indexes (e.g. the frequency indexes $N_1$ or $N_3$) is smaller than a threshold, the processing unit 14 may estimate a heart rate according to a variation tendency of the heart rate indexes $N_{HR}$ corresponding to a plurality of the detection periods.

For example, it is assumed that the threshold is 10 and the heart rate index $N_{HR}$ varies from 73 to 110 after the period. In this case, a difference value between the heart rate index $N_{HR}$ and the residual index 117 (i.e. the frequency index $N_3$) is 7, which is smaller than the threshold, and the processing unit 14 then estimates a heart rate according to the variation tendency of the heart rate indexes $N_{HR}$ corresponding to a plurality of the detection periods, wherein the heart rate calculation method according to the variation tendency and the frequency indexes is described above, and thus details thereof are not repeated herein.

In the above embodiments, the PPG signal $S_p$ of the PPG measuring device 10 and the acceleration signal $S_a$ of the motion sensor 12 are not only configured to calculate a heart rate. The processing unit 14 further calculates a physiology state and exercise data (e.g. step counting, running/riding velocity calculation, and sport time recording) according to the PPG signal $S_p$ and the acceleration signal $S_a$ according to different applications.

In the descriptions that follow, the present disclosure will be described in reference to embodiments that describe heart rate detection architecture. However, the embodiments of the present disclosure are not limited to any particular environment, application or implement. Therefore, the descriptions of the embodiments that follow are for purposes of illustration but not limitation. It is understood that elements indirectly related to the present disclosure are omitted and are not shown in the following embodiments and drawings.

The following figures show several examples of the present disclosure, which is suitable in wearable heart rate detection devices. That is, the wearable heart rate detection device using the present disclosure shown below is intended to be placed on the limb(s) or body of a human being to detect a heart rate by PPG module. People skilled in the art know well the functions of conventional wearable devices, and redundant explanation is omitted hereinafter.

Figure 9:
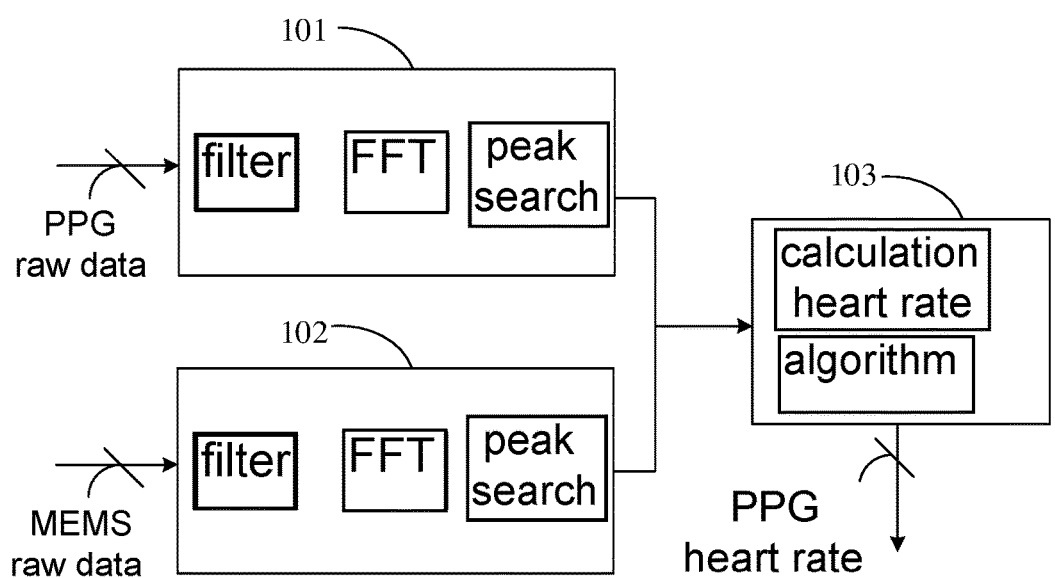
FIG. 9 is a schematic block diagram of a heart rate detection architecture of the present disclosure.

FIG. 9 is a block diagram of heart rate detection architecture. The heart rate detection architecture includes a PPG hardware module 101, a MEMS hardware module 102, and a microcontroller unit (MCU) 103 electrically coupled to the PPG hardware module 101 and the MEMS hardware module 102. The PPG hardware module 101 is configured to receive and filter PPG raw data for digital process. In this embodiment, Fast Fourier Transformation (FFT) is applied to complete the digital process and generate a frequency distribution result, or referred as PPG frequency data. The frequency distribution result includes many frequency values, and sometimes the frequency distribution result is a continuous frequency distribution. Among these frequency values, there are several peak values comparing with the rest, e.g., referring to FIG. 4A. One of the peak values represents a heart rate, and the MCU 103 is configured to calculate these peak values to find out the frequency representing the heart rate.

The MCU 103 is also configured to generate a confidence level of the frequency distribution result. The confidence level is directly related to the heart rate calculation result and would be outputted as well for later process. For example, the corresponding algorithm can determine whether or not to adopt the heart rate result based on the confidence level. Or the corresponding algorithm can also be designed to ignore the confidence level and just adopt the heart rate result. The confidence level indicates a signal grade or quality of the PPG frequency data. The higher the confidence level is, the better the signal grade of the PPG frequency data. For example, if the PPG frequency data has only one peak value larger than a predetermined threshold, the confidence level is set as the highest. If the PPG frequency data has several peak values larger than the predetermined threshold, the confidence level is set to be smaller. If the PPG frequency data has no peak value larger than the predetermined threshold, the confidence level is set as smallest. In some embodiments, the confidence level is indicated by the indication unit 18 as shown in FIG. 1.

For example, the PPG hardware module 101 includes a first bandpass filter (e.g., the filter 16 in FIG. 1), a first conversion module (e.g., the module 140 in FIG. 1) and a first peak extraction module (e.g., the module 142 in FIG. 1), and the PPG hardware module 101 is configured to receive the PPG raw data from a PPG detector (e.g., the device 10 in FIG. 1). The first bandpass filter is configured to filter the PPG raw data, e.g., using a pass band between 0.5 Hz and 4 Hz, but not limited thereto. The first conversion module is configured to convert the PPG raw data to PPG frequency data (e.g., frequency domain PPG signal mentioned above), e.g., using Fast Fourier Transform, but not limited thereto. The first peak extraction module is configured to search PPG peak values among the PPG frequency data, e.g., referring to FIG. 4A, and output the PPG peak values (e.g., frequencies associated with the peak values) and the PPG frequency data to the MCU 103. The filtering, time-frequency conversion and peak searching of the PPG hardware module 101 have been illustrated above, and thus details thereof are not repeated herein.

The MEMS hardware module 102 is configured to receive MEMS raw data. The MEMS raw data represents the motion status of a human being, i.e. a user wearing the heart rate detection device. When the user moves his/her body or limb(s), the motion would some degree shake the wearable heart rate detection device and generate some strong frequency signal when the PPG hardware module 101 is generating said peak values. If the peak values caused by the motion are too strong, it may influence the later calculation done by the MCU 103 and result in generating wrong heart rate values. The MEMS hardware module 102 can take the MEMS raw data for digital process, such as the FFT process to generate MEMS frequency data (e.g., frequency domain acceleration signal mentioned above), to generate some peak frequency values representing the motion of user. The peak values can be applied for later calculation to correct, adjust or estimate heart rate calculation. The MCU 103 estimates a heart rate according to the PPG frequency data in referencing the MEMS frequency data. For example, the peak values generated by the MEMS hardware module 102 can be used to eliminate the peak values generated by the PPG hardware module 101 with the same frequency, e.g., referring to FIG. 6. In some cases, if the architecture determines that the heart rate is similar or equal to the peak frequency value related to the motion of user, the architecture can also not to eliminate the peak value generated by the MEMS hardware module 102. Or the architecture can take the peak values generated by the MEMS hardware module 102 as a reference for generating the confidence level. The use of peak values generated by the MEMS hardware module 102 can be various depending on the algorithms.

For example, the MEMS hardware module 102 includes a second bandpass filter (e.g., the filter 16 in FIG. 1), a second conversion module (e.g., the module 140 in FIG. 1) and a second peak extraction module (e.g., the module 142 in FIG. 1), and the MEMS hardware module 102 is configured to receive the MEMS raw data from a MEMS accelerometer (e.g., the sensor 12 in FIG. 1). The second bandpass filter is configured to filter the MEMS raw data, e.g., using a pass band of 0.5 Hz and 4 Hz, but not limited thereto. The second conversion module is configured to convert the MEMS raw data to MEMS frequency data, e.g., using Fast Fourier Transform, but not limited thereto. The second peak extraction module is configured to search MEMS peak values (e.g., referring to FIG. 5A) among the MEMS frequency data, and output the MEMS peak values (e.g., frequencies associated with the peak values) and the MEMS frequency data to the MCU 103.

In another embodiment, the PPG hardware module 101 and MEMS hardware module 102 are configured to output many parameters for later calculation depending on different system designs. This can be called as hardware acceleration function since the hardware modules (i.e. the PPG hardware module 101 and the MEMS hardware module 102) can directly output parameters without MCU operation. The parameters includes, for example, PPG peak values, MEMS peak values, PPG FFT output, MEMS FFT output, PPG filter output, and MEMS filter output.

For example, the aforementioned parameters can be applied for airborne detection. When the wearable device is taken off from the limb(s) or body, the PPG detection should be ceased to prevent continuously outputting data. On the other hand, when the wearable device is placed on the limb(s) or body, the PPG detection should be activated. Both the PPG hardware module 101 and MEMS hardware module 102 can be applied for airborne detection. For example, when the wearable device is taken off from the limb(s), the PPG hardware module 101 is unable to receive normal PPG raw data. If the status continues for a certain period, then the output of the PPG hardware module 101 can be adapted to indicate the airborne status. For the MEMS hardware module 102, when the wearable device is taken off from the limb(s), the MEMS raw data may indicate a rapid and huge motion, and the output of the MEMS hardware module 102 can be adapted to indicate the airborne status too. The outputs of the PPG hardware module 101 and MEMS hardware module 102 can be jointly or independently considered for airborne determination. Similarly, when the wearable device is placed on limb(s), the PPG hardware module 101, for example, can receive significant PPG raw data indicating the status. Or the MEMS hardware module 102 can receive MEMS raw data indicating a significant motion followed by a relative steady or weak motion.

It is important to tell the airborne status and the placed-on status, especially for power saving issue. If the wearable device is not placed on the limb(s), then the wearable device can stay in stand-by mode or power saving mode to only keep essential hardware consuming power instead of whole device. The PPG hardware module 101 and MEMS hardware module 102 can be applied for airborne status and/or placed-on status detection. In other embodiment, the PPG hardware module 101 and MEMS hardware module 102 can jointly be operated with other elements, such as ambient light sensor, touch sensor, and etc., to detect the airborne status and/or placed-on status. The MCU 103 is machine trained previously to recognize said taken-off and placed-on statuses. In some embodiments, said taken-off and placed-on statuses are indicated by the indication unit 18 in FIG. 1.

In addition, the MEMS hardware module 102 can be applied to determine the motion type of a user, such as the run, indoor walk, outdoor walk, upper limb wave, lower limb wave, swimming, cycling and walk plus run. When the user moves different limb(s) or the body, MEMS detection would generate different MEMS raw data corresponding to different motions. Generally, when the motion carries more energy, it would cause larger reaction in MEMS detection and result in significant peak value at certain frequency after processed by the MEMS hardware module 102. The MCU 13 is machine trained to recognize different MEMS frequency data according to the comparison between currently detected MEMS frequency data and previously categorized (i.e. corresponding to different motion types mentioned above) frequency data. One method to recognize a sport state is referred to U.S. patent application Ser. No. 15/231, 690, filed on Aug. 8, 2016, assigned to the same assignee of the present disclosure, and the full disclosure of which is incorporated herein by reference.

Furthermore, in order to reduce the cost, circuit complexity and circuit board size, the heart rate detection device of the present disclosure employs an adjustable oscillator instead of a crystal oscillator. However, an oscillation frequency of the adjustable oscillator may not be correct such that the calculated heart rate by the MCU 103 has a deviation from an actual heart rate of the user. Accordingly, the MCU 103 further calibrates the estimated or calculated heart rate according to a local oscillation frequency of an adjustable local oscillator of the heart rate detection device and an external oscillation frequency received from an external host, e.g., a cell phone or a computer system for receiving and using the estimated or calculated heart rate. In this embodiment, said external oscillation frequency is a correct clock signal used to calibrate the estimated or calculated heart rate which is obtained based on the local oscillation frequency of the heart rate detection device. When the local oscillation frequency of the heart rate detection device is faster or slower than the external oscillation frequency of the external host, the calculated heart rate is calibrated according to a difference or a ratio between the local oscillation frequency and the external oscillation frequency. Methods of calibrating the estimated or calculated heart rate are referred to U.S. patent application Ser. No. 14/728,051, filed on Jun. 2, 2015, assigned to the same assignee of the present disclosure, and the full disclosure of which is incorporated herein by reference.

Figure 11:
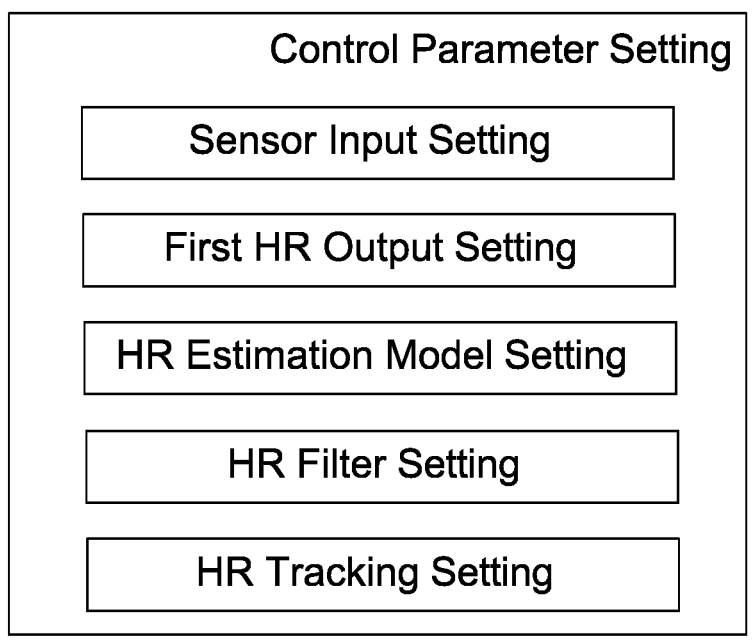
FIG. 11 is a schematic block diagram of the control parameter setting of the present disclosure.

Alternatively, the MCU 103 performs device setting control for controlling the operation of heart rate detection device, e.g., a sensor input setting, a first heart rate (HR) output setting, a heart rate estimation model setting, a heart rate filter setting and a heart rate tracking setting as shown in FIG. 11.

The sensor input setting is, for example, to set the sample rate or a number of sampled dots of the PPG hardware module 101 and the MEMS hardware module 102. The MCU 103 generates a control signal to change said sensor input setting.

The first heart rate output setting is, for example, to set a time interval between a start time of the detection device and an output time of generating a heart rate. Under some conditions, the heart rate detection device needs to take a longer time to calculate a heart rate according to the PPG raw data, e.g., during a placed-on status. However, the MCU 103 still outputs a heart rate even the heart rate is not calculated according to the PPG raw data. For example, the MCU 103 outputs a general heart rate according to the motion type and/or historic data of a user that are recorded in a memory of the heart rate detection device when the heart rate is not obtainable according to the PPG raw data. Changing the first heart rate output setting changes the correctness or confidence level of the outputted heart rate as well.

Figure 13:
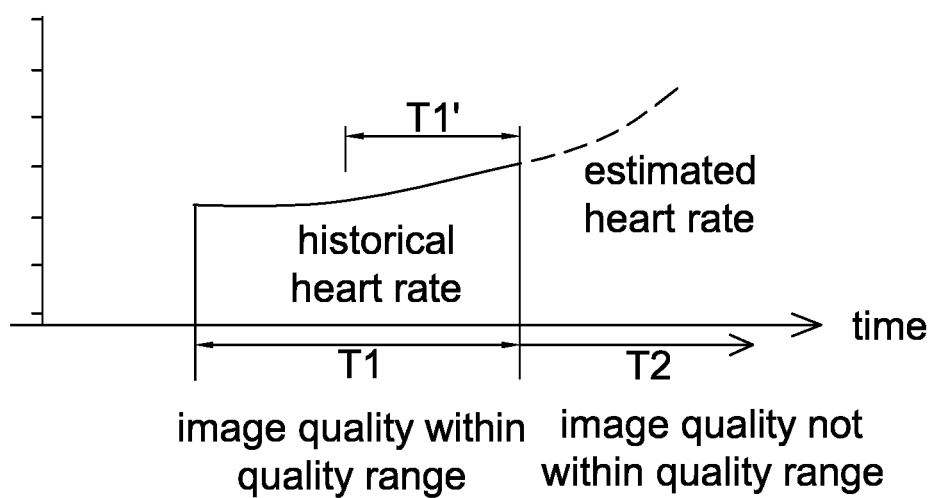
FIG. 13 is a schematic diagram of a heart rate variation including calculated heart rates and estimated heart rates.

The heart rate estimation model setting is, for example, to change the estimated heart rate when the heart rate is not directly obtainable according to the detected PPG raw data, e.g., referring to U.S. patent application Ser. No. 15/231, 690. For example, when the user starts to exercise (e.g., during T1 in FIG. 13), the MCU 103 initially detects that the heart rate is increasing at a specific rate which has a specific slope. However, during the exercise, the heart rate detection device is not able to detect the PPG signal anymore due to the relative movement between the heart rate detection device and the detected skin. The MCU 103 of the present disclosure still outputs the estimated heart rate (e.g., during T2 in FIG. 13) according to the trend of the heart rate detected previously (e.g., during T1' in FIG. 13). By changing the heart rate estimation model setting, the trend of the estimated heart rate is changed. In this embodiment, the estimated heart rate is referred to a heart rate estimated according to the historical heart rate in referencing the motion type of the user.

The heart rate setting is, for example, to set the pass band of the bandpass filters of the PPG hardware module 101 and the MEMS hardware module 102. The MCU 103 changes the range, e.g., 0.5 Hz to 4 Hz, according to different applications. For example, when a motion type such as a sport state is detected, the MCU 103 can change the range to be between 1.5 Hz and 4 Hz. For example, when a motion type such as a sleep state is detected, the MCU 103 can change the range to be between 0.5 Hz and 3 Hz.

The heart rate track setting is, for example, to set a tracking response of the heart rate. For example, when the MCU 103 changes the estimated (guessed) heart rate to the calculated (real) heart rate (i.e. calculated according to the obtained PPG raw data), the MCU 103 is set to directly or in a step-by-step manner to change from the estimated heart rate to the calculated heart rate if there is an apparent difference therebetween. Changing the heart rate track setting is referred to, for example, changing a step interval to trace the calculated heart rate.

For example, the above motion state is configured to determine at least one of the heart rate estimation model setting and the heart rate tracking setting. If the motion state is a sport state, the increasing trend (e.g., slope) of the heart rate determined by the heart rate estimation model is higher, and the heart rate tracking speed is faster. On the contrary, if the motion state is a rest state, the increasing trend (e.g., slope) of the heart rate determined by the heart rate estimation model is smaller or close to zero, and the heart rate tracking speed is slower. The control parameter setting is used to change the outputted heart rate feature, e.g., by changing parameters used in operation algorithms, corresponding to different requirements.

Figure 12:
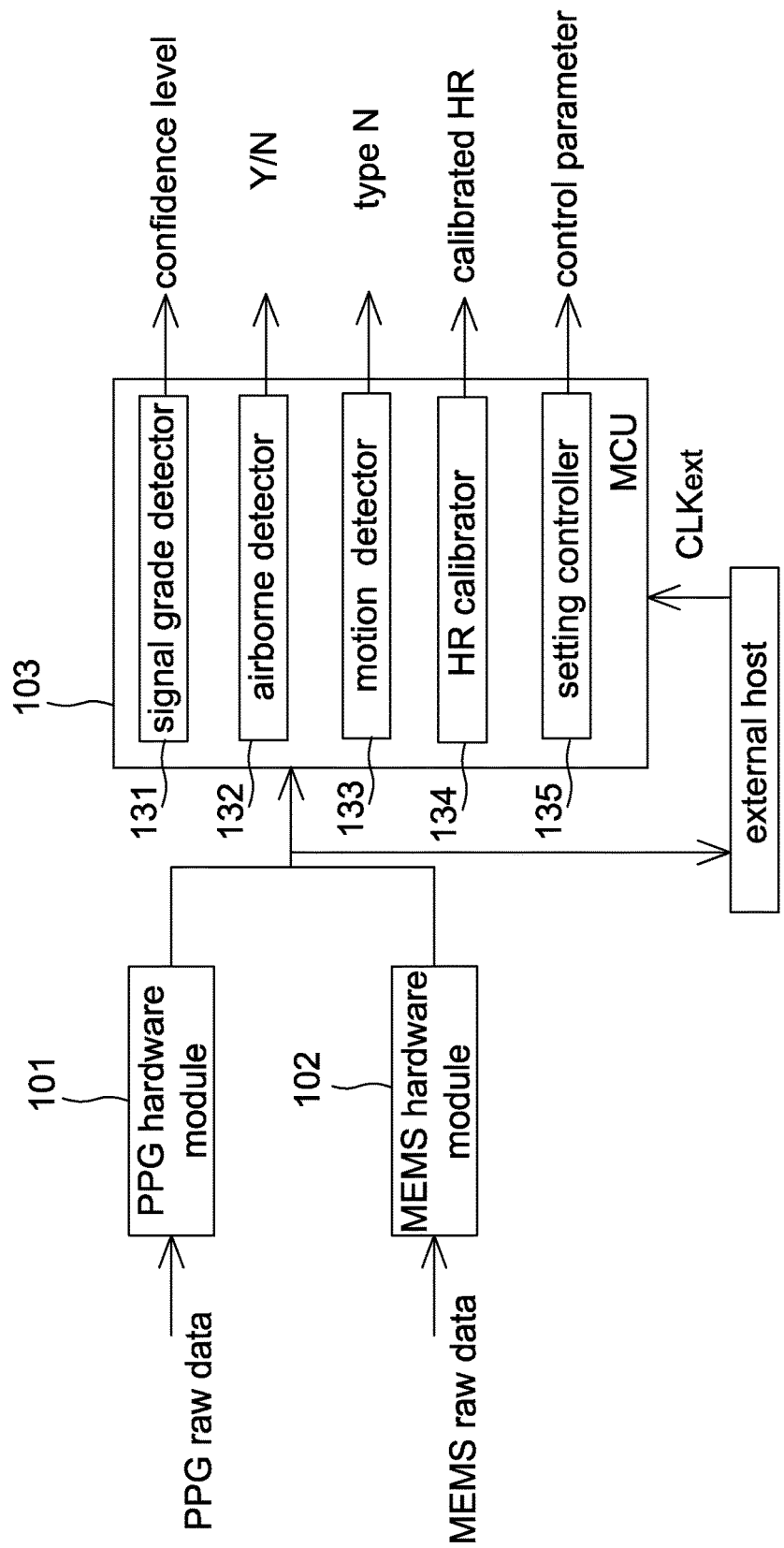
FIG. 12 is a schematic block diagram of heart rate detection architecture according to another embodiment of the present disclosure.

FIG. 12 is a schematic block diagram showing that the MCU 13 operates different functions mentioned above according to the parameters received from the PPG hardware module 101 and MEMS hardware module 102. For example, the MCU 13 includes at least one of a signal grade detector 131 for detecting and outputting a confidence level, an airborne detector 132 for detecting and outputting an airborne status or placed-on status, a motion detector 133 for detecting and outputting a motion type, a HR calibrator 134 for correcting the heart rate generated according to the detected PPG raw data, and a setting controller 135 for setting the detecting and operating control parameters of the heart rate detection device. The operation of the above function blocks 131-135 are implemented by hardware, firmware or a combination thereof.

In other embodiments, the operations performed by at least a part of the functional blocks 131-135 are performed by an external host which includes a central processing unit (CPU), microcontroller unit (MCU) or an application specific integrated circuit (ASIC) to share the loading of the MCU 103. More specifically, the parameters from the PPG hardware module 101 and from the MEMS hardware module 102 are outputted to more than one devices or chips to perform the heart rate calculation, the heart rate calibration, the signal grade determination, the airborne detection, the motion detection and/or the parameter setting as mentioned above.

FIGS. 10*a*-10*d* are various embodiments of the connection structure among the PPG hardware module 101, MEMS hardware module 102 and MCU 103.

Figure 10A:
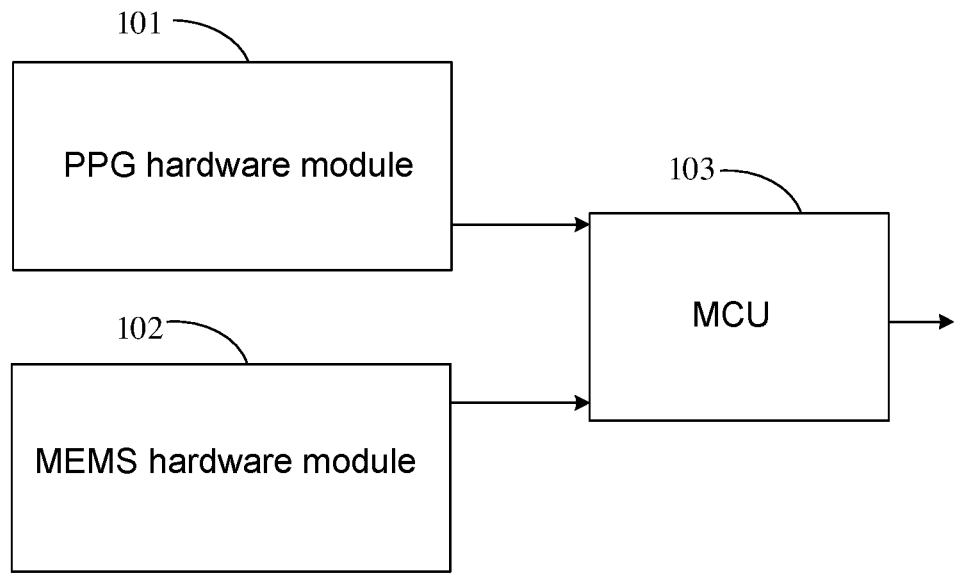
FIGS. 10a-10d are various embodiments of the connection structure among a PPG hardware module, a MEMS hardware module, and an MCU of the present disclosure.

FIG. 10*a* shows a common connection structure. The PPG hardware module 101 and the MEMS hardware module 102 are separately connected to the MCU 103. In this embodiment, the MCU 103 requests data from two modules to send the PPG frequency data and the MEMS frequency data respectively, and the two modules do not communicate with each other.

Figure 10B:
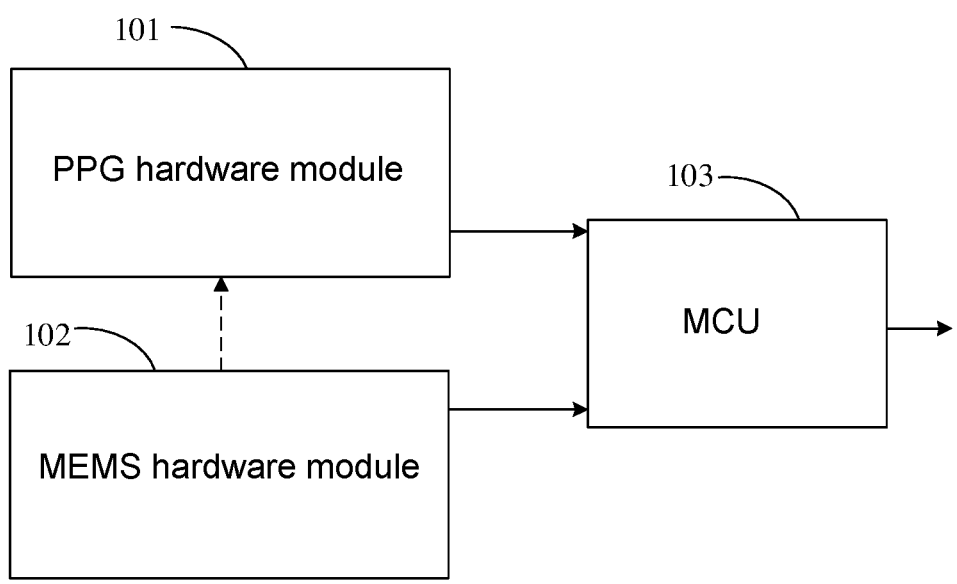

FIG. 10*b* shows another embodiment, the PPG hardware module 101 is configured to request data or monitor data from the MEMS hardware module 102 and provide PPG data together with MEMS data in response to the MCU 103 request. In some embodiments, the PPG hardware module 101 receives the MEMS raw data from the MEMS hardware module 102 at first, and then PPG hardware module 101 (e.g., the first conversion module thereof) converts the MEMS raw data to MEMS frequency data to be sent to the MCU 103. In this embodiment, the PPG hardware module 101 converts the received MEMS raw data to MEMS frequency data at first, and then the MCU 103 receives both the PPG frequency data and the MEMS frequency data from the PPG hardware module 101. In this embodiment, the MEMS hardware module 102 may or may not perform the FFT and peak searching according to different applications. Also the MCU 103 can directly request data (e.g., the MEMS frequency data) from MEMS hardware module 102. In other embodiments, the PPG hardware module 101 receives the MEMS frequency data from the MCU 103 to filter the PPG frequency data (e.g., referring to FIG. 6). The PPG hardware module 101 outputs the filtered PPG frequency data to the MCU 103.

Figure 10C:
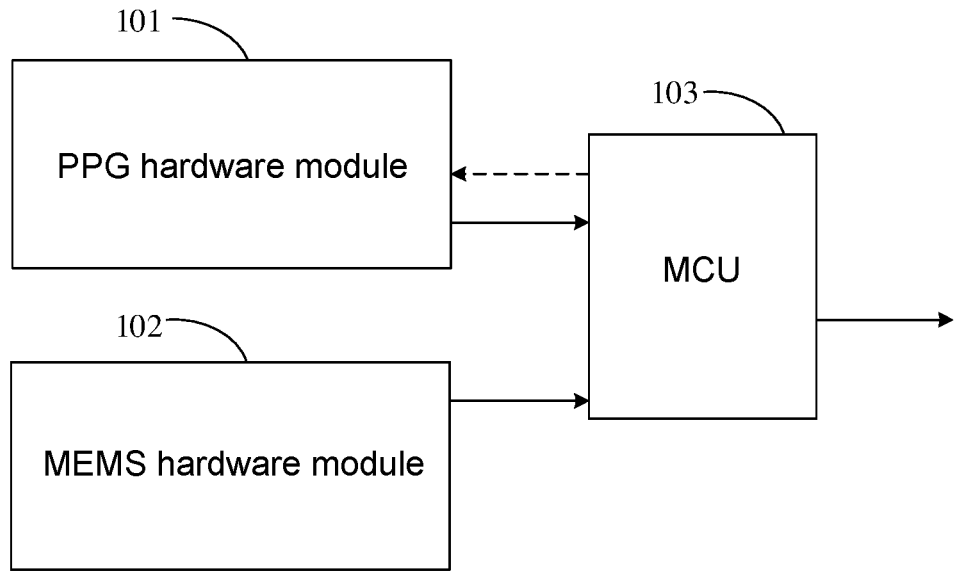

FIG. 10*c* shows another embodiment, the PPG hardware module 101 is configured to request data from the MCU 103 as a hub or using the data from the MCU 103 for correction. The rest connection of FIG. 10*c* is the same as FIG. 10*a*. In some embodiments, the PPG hardware module 101 receives the MEMS raw data from the MEMS hardware module 102 via the MCU 103 at first, and then the PPG hardware module 101 (e.g., the first conversion module thereof) converts the MEMS raw data to MEMS frequency data to be sent to the MCU 103. In this embodiment, the MCU 103 receives both the PPG frequency data and the MEMS frequency data from the PPG hardware module 101. In this embodiment, the MEMS hardware module 102 may or may not perform the FFT and peak searching according to different applications. In other embodiments, the PPG hardware module 101 receives the MEMS frequency data from the MCU 103 to filter the PPG frequency data (e.g., referring to FIG. 6). The PPG hardware module 101 outputs the filtered PPG frequency data to the MCU 103.

Figure 10D:
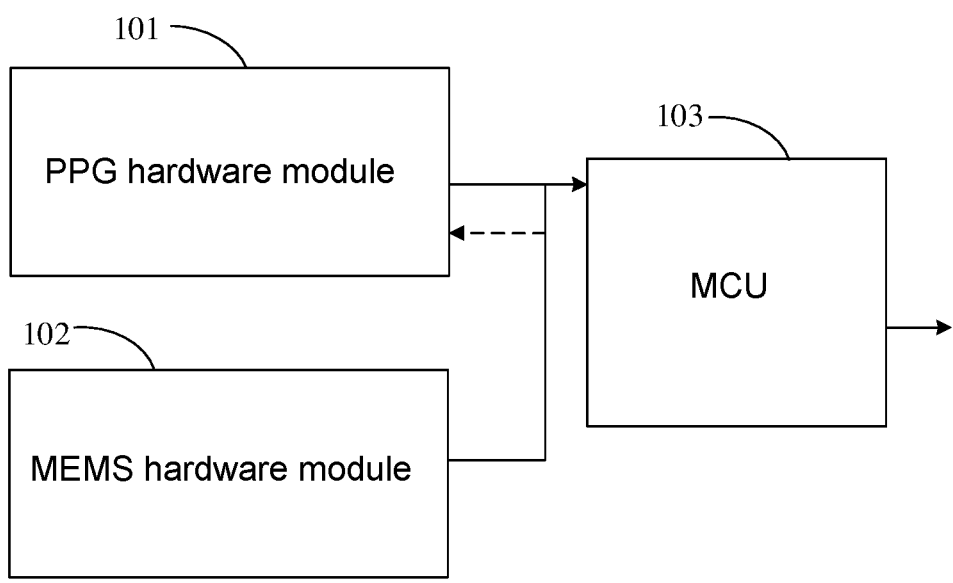

FIG. 10*d* shows another embodiment, the PPG hardware module 101 is connected to the MEMS hardware module 102 first, then the two modules jointly transmit data to the MCU 103 in response to the MCU 103 request. Also the PPG hardware module 101 is configured to request data or monitor data from the MEMS hardware module 102. In some embodiments, the MEMS hardware module 102 sends the MEMS raw data to a bus line at first, the PPG hardware module 10 receives the MEMS raw data from the bus line to convert (e.g., the first conversion module thereof) the received MEMS raw data to MEMS frequency data, and then the MCU 103 receives both the PPG frequency data and the MEMS frequency data from the PPG hardware module 101. In this embodiment, the MEMS hardware module 102 may or may not perform the FFT and peak searching according to different applications. In other embodiments, the PPG hardware module 101 receives the MEMS frequency data from the bus line to filter the PPG frequency data (e.g., referring to FIG. 6). The PPG hardware module 101 outputs the filtered PPG frequency data to the MCU 103.

The connection protocol of aforementioned embodiments can be I2C, SPI, SMBUS or other protocols without particular limitations.

It should be mentioned that although FIGS. 9 and 10*a*-10*d* show that the PPG hardware module 101, the MEMS hardware module 102 and the MCU 103 are three functional blocks, they are only intended to illustrate but not to limit the present disclosure. For example, the PPG hardware module 101 and the MEMS hardware module 102 respectively include a digital signal processor (DSP) for performing the filtering, time-frequency conversion and peak searching. In other embodiments, the three functional blocks are all integrated in the MCU 103 to form one package, and said one package performs all the operations of the PPG hardware module 101, the MEMS hardware module 102 and the MCU 103 mentioned above after receiving the PPG raw data from an external PPG detector and the MEMS raw data from an external MEMS accelerometer.

The aforementioned embodiments are described for people skilled in the art to know the flexibility and ability among various connection structure. People skilled in the art can modify or arrange similar connection based on knowledge of aforementioned embodiments.

What is claimed is:
1. A heart rate detection device, comprising:
a photoplethysmography (PPG) hardware module configured to receive PPG raw data and comprising a bandpass filter configured to filter the PPG raw data, the PPG hardware module further configured to generate PPG frequency data and first frequency domain information comprising a first frequency index set and a first spectrum value set associated with the first frequency index set;
a microelectromechanical systems (MEMS) hardware module configured to receive MEMS raw data and comprising a bandpass filter to filter the MEMS raw data, the MEMS hardware module further configured to generate MEMS frequency data and second frequency domain information including a second frequency index set and a second spectrum value set associated with the second frequency index set; and
a microcontroller unit (MCU), electrically coupled to the PPG hardware module and the MEMS hardware mod- ule, and configured to estimate a heart rate according to the PPG frequency data in referencing the MEMS frequency data by determining a reference index according to a frequency index corresponding to a spectrum peak value in the second frequency domain information, determining a denoising parameter according to the reference index, removing spectrum values in the first frequency domain information corresponding to the reference index and nearby reference indexes according to the denoising parameter to generate denoised first frequency domain information, and calculating the heart rate according to a spectrum peak value of the denoised first frequency domain information, wherein the PPG hardware module and the MEMS hardware module respectively output the PPG frequency data and the MEMS frequency data without MCU operation to share loading of the MCU, and wherein the estimated heart rate is configured to be shown on a display.

2. The heart rate detection device as claimed in claim 1, wherein the MCU is further configured to calibrate the estimated heart rate according to a local oscillation frequency of the heart rate detection device and an external oscillation frequency received from an external host.

3. The heart rate detection device as claimed in claim 1, wherein the MCU is further configured to generate a confidence level of the PPG frequency data, wherein the confidence level depends on a number of peak values in the PPG frequency data larger than a predetermined threshold.

4. The heart rate detection device as claimed in claim 1, wherein the MCU is further configured to determine an airborne status according to at least one of the PPG frequency data and the MEMS frequency data.

5. The heart rate detection device as claimed in claim 1, wherein the MCU is further configured to perform at least one of a sensor input setting, a first heart rate output setting, a heart rate estimation model setting, a heart rate filter setting and a heart rate tracking setting.

6. The heart rate detection device as claimed in claim 5, wherein the MCU is further configured to output a motion state according to the MEMS frequency data.

7. The heart rate detection device as claimed in claim 6, wherein the motion state is configured to determine at least one of the heart rate estimation model setting and the heart rate tracking setting.

8. The heart rate detection device as claimed in claim 1, wherein
the PPG hardware module is further configured to receive the MEMS raw data from the MEMS hardware module to convert the received MEMS raw data to the MEMS frequency data at first, and then
the MCU is further configured to receive both the PPG frequency data and the MEMS frequency data from the PPG hardware module.

9. The heart rate detection device as claimed in claim 1, wherein
the PPG hardware module is further configured to receive the MEMS raw data from the MEMS hardware module via the MCU to convert the received MEMS raw data to the MEMS frequency data at first, and then
the MCU is further configured to receive both the PPG frequency data and the MEMS frequency data from the PPG hardware module.

10. The heart rate detection device as claimed in claim 1, wherein
the MEMS hardware module is configured to send the MEMS raw data to a bus line at first,
the PPG hardware module is further configured to receive the MEMS raw data from the bus line to convert the received MEMS raw data to the MEMS frequency data, and then
the MCU is further configured to receive both the PPG frequency data and the MEMS frequency data from the PPG hardware module.

11. The heart rate detection device as claimed in claim 1, wherein the PPG hardware module is further configured to search peak values among the PPG frequency data.

12. The heart rate detection device as claimed in claim 1, wherein the MEMS hardware module is further configured to search peak values among the MEMS frequency data.

13. A heart rate detection device, configured to receive a photoplethysmography (PPG) raw data from a PPG detector and a microelectromechanical systems (MEMS) raw data from a MEMS accelerometer, the heart rate detection device comprising:

a PPG hardware module configured to receive the PPG raw data, the PPG hardware module comprising:
a first bandpass filter configured to filter the PPG raw data;
a first conversion module configured to convert the filtered PPG raw data to PPG spectrum values and PPG frequency index; and
a first peak extraction module configured to search PPG peak spectrum values among the PPG spectrum values, and output the PPG peak spectrum values and the PPG frequency index;

a MEMS hardware module configured to receive the MEMS raw data, the MEMS hardware module comprising:
a second bandpass filter configured to filter the MEMS raw data;
a second conversion module configured to convert the filtered MEMS raw data to MEMS spectrum values and MEMS frequency index; and
a second peak extraction module configured to search a MEMS peak spectrum value among the MEMS spectrum values, and output the MEMS peak spectrum values and the MEMS frequency index; and a microcontroller unit (MCU), electrically coupled to the PPG hardware module and the MEMS hardware module, and configured to estimate a heart rate according to the PPG peak spectrum values, the PPG frequency index, the MEMS peak spectrum values and the MEMS frequency index by
determining a reference index according to a frequency index corresponding to the MEMS peak spectrum value in the MEMS spectrum values,
determining a denoising range according to the reference index,
removing the PPG spectrum values in the PPG spectrum values corresponding to the denoising range to generate denoised PPG frequency data, and
calculating the heart rate according to a PPG peak spectrum value of the denoised PPG frequency data, wherein the PPG hardware module outputs the PPG peak spectrum values as well as the PPG frequency index and the MEMS hardware module outputs the MEMS peak spectrum value as well as the MEMS frequency index without MCU operation to share loading of the MCU, and wherein the estimated heart rate is configured to be shown on a display.

14. The heart rate detection device as claimed in claim 13, wherein the first and second conversion modules are configured to perform fast Fourier transform.

15. The heart rate detection device as claimed in claim 13, wherein a pass band of the first and second bandpass filters is between 0.5 Hz and 4 Hz.

* * * * *